United States Patent
Scott et al.

(10) Patent No.: US 9,820,759 B1
(45) Date of Patent: Nov. 21, 2017

(54) DRILL GUIDE FOR USE IN BONE FIXATION

(71) Applicants: Joshua Scott, Houston, TX (US);
Perry Forrester, Houston, TX (US)

(72) Inventors: Joshua Scott, Houston, TX (US);
Perry Forrester, Houston, TX (US)

(73) Assignee: Ascension Orthopedics, Inc., Austin, TX (US)

( * ) Notice: Subject to any disclaimer, the term of this patent is extended or adjusted under 35 U.S.C. 154(b) by 580 days.

(21) Appl. No.: 13/897,511

(22) Filed: May 20, 2013

(51) Int. Cl.
*A61B 17/17* (2006.01)
*A61B 17/66* (2006.01)
*A61B 17/02* (2006.01)
*A61B 17/064* (2006.01)
*A61B 17/68* (2006.01)

(52) U.S. Cl.
CPC .......... *A61B 17/17* (2013.01); *A61B 17/1775* (2016.11); *A61B 17/1796* (2013.01); *A61B 17/025* (2013.01); *A61B 17/0642* (2013.01); *A61B 17/66* (2013.01); *A61B 2017/681* (2013.01)

(58) Field of Classification Search
CPC ... A61B 17/66; A61B 17/8019; A61B 17/025; A61B 17/0642; A61B 17/681; A61B 17/0256–17/0275; A61B 17/0206
USPC ....... 606/96, 97, 98; 408/110, 115 R, 115 B, 408/72 B
See application file for complete search history.

(56) References Cited

U.S. PATENT DOCUMENTS

| | | | | |
|---|---|---|---|---|
| 2,779,218 A * | 1/1957 | Edgerton | .............. | B23B 49/005 408/110 |
| 5,382,250 A * | 1/1995 | Kraus | ................ | A61B 17/1695 408/202 |
| 5,989,025 A * | 11/1999 | Conley | ................ | A61B 17/176 408/241 B |
| 6,261,296 B1 * | 7/2001 | Aebi | .................... | A61B 17/025 600/219 |
| 8,323,292 B2 * | 12/2012 | Dudasik | .............. | A61B 17/025 606/105 |
| 2002/0133157 A1 * | 9/2002 | Sterett | ................ | A61B 17/8095 606/286 |
| 2008/0242937 A1 * | 10/2008 | DiNucci | .............. | A61B 17/025 600/201 |
| 2011/0098757 A1 * | 4/2011 | Schelling | ........... | A61B 17/7079 606/324 |
| 2011/0264149 A1 * | 10/2011 | Pappalardo | ........ | A61B 17/8019 606/286 |
| 2011/0288595 A1 * | 11/2011 | Niederberger | ..... | A61B 17/8019 606/286 |
| 2014/0031828 A1 * | 1/2014 | Patel | .................... | A61B 17/025 606/90 |

\* cited by examiner

*Primary Examiner* — Matthew Lawson
*Assistant Examiner* — Amy Sipp
(74) *Attorney, Agent, or Firm* — Bushman Werner, P.C.

(57) ABSTRACT

A universal drill guide for use in position the location of holes to be drilled for insertion of bone staples. The drill guide has first and second legs pivotally secured to one another and first and second jaw members, each of the jaw members being provided with a drill guide. An indexer connected to the first and second legs includes a biaser, e.g., a spring to bias the first and second legs in a direction away from one another and a latch, catch or the like for selectively, releasably holding the first and second legs in a predetermined desired spacing.

20 Claims, 3 Drawing Sheets

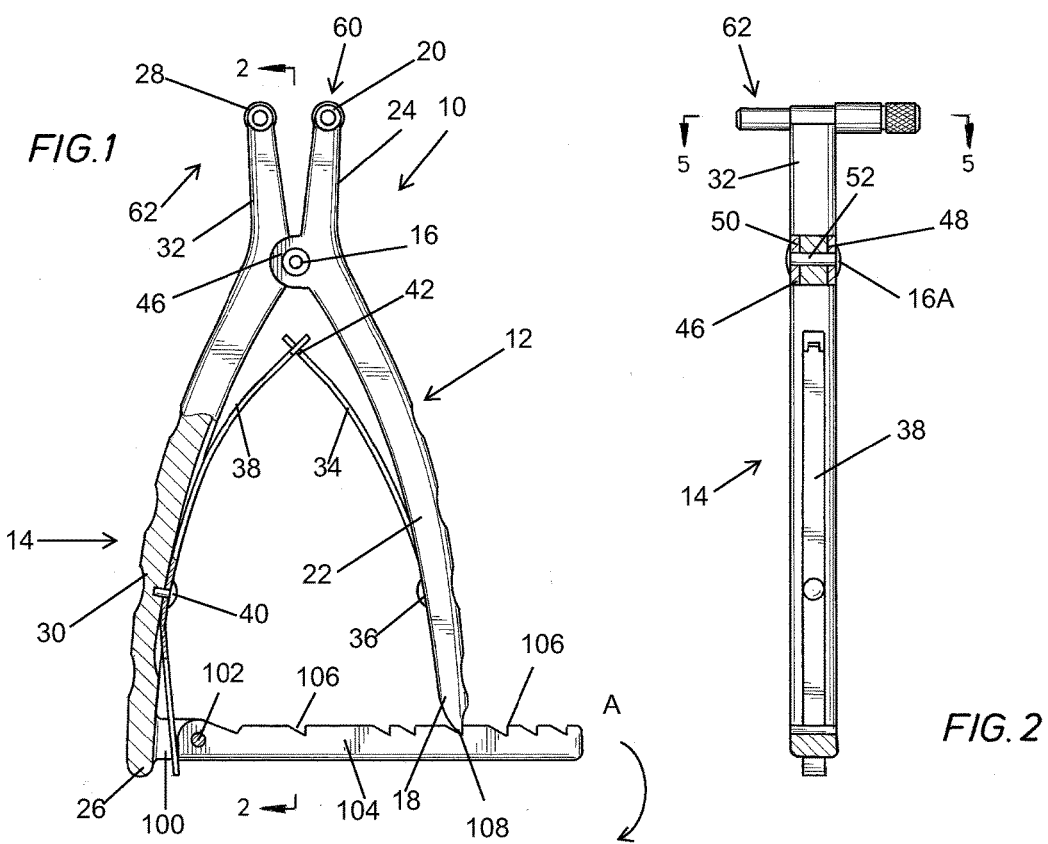

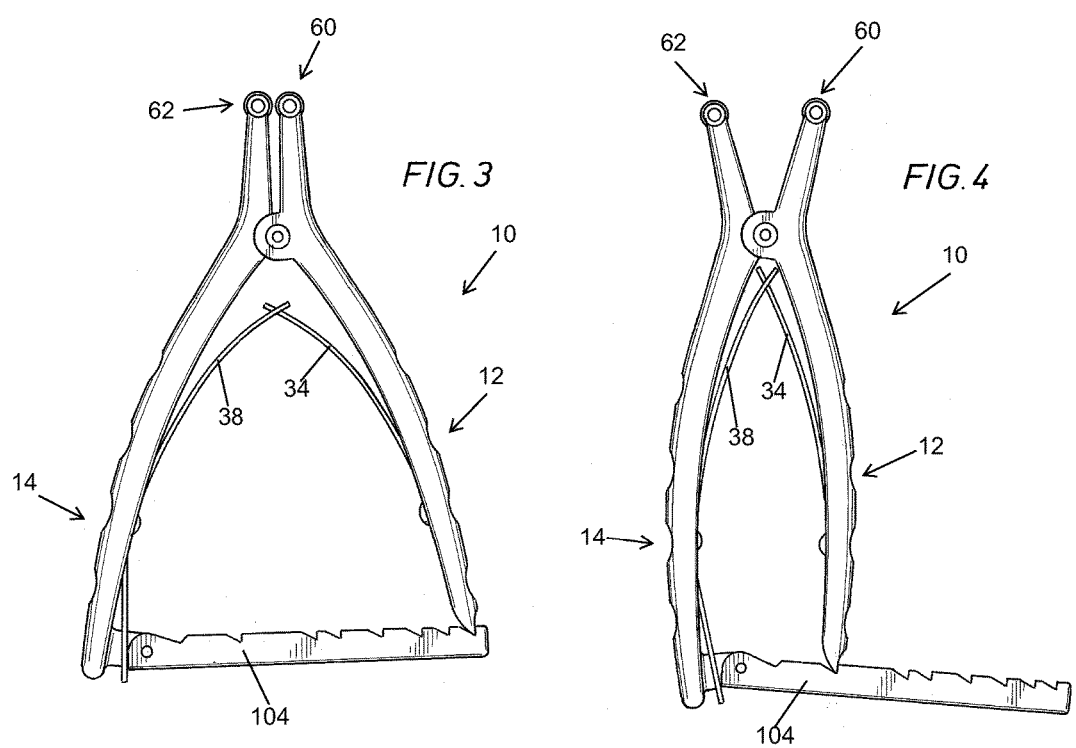

DRILL GUIDE FOR USE IN BONE FIXATION

FIELD OF THE INVENTION

The present invention relates to bone fixation surgery and, more particularly, to drill guides used to position the location of holes to be drilled for the insertion of bone staples.

BACKGROUND OF THE INVENTION

Bone staples are widely used in bone fixation surgery and in particular in foot and ankle surgery. The use of bone staples is considered to be an effective internal fixation method. The advantages of bone staples include easier fixation of bones, reduced surgical time and trauma which in turn leads to improved healing and reduced postoperative pain.

Various types of bone staples are available, differing in shape and physical properties. Recently bone staples have been introduced based on shape memory materials.

Shape memory bone staples find application in a variety of bone surgery techniques, including without limitation, osteotomies of the first phalanx of the foot, arthrodesis of the first metatarsal phalangeal joint, etc. Regardless of the surgical procedure, and when using memory metal bone staples, it is necessary for two holes to be drilled at appropriate locations of the bone(s) such that when the memory metal staples are inserted into the holes, the staples exert the proper amount of compression. Furthermore, bone staples vary in width depending upon the procedure in which they are being used. This necessitates both selection of the proper staple size as well as precise locating of the holes in the bones in which the legs of the staple are placed.

Prior art drill guides used with bone staples generally comprise a blade with multiple holes or guide bores, the spacing between the holes corresponding to typical staple sizes. Other drill guides generally comprise blocks having holes therethrough, the spacing of the holes corresponding to the staple size to be used. With respect to the use of these drill guides formed of blocks, it is generally necessary to have a different block or drill guide for each sized staple.

SUMMARY OF THE INVENTION

In one aspect, the present invention provides an adjustable drill guide for use in bone fixation surgical procedures.

In another aspect, the present invention provides a drill guide for use with memory staples or other compression type fixation devices used in bone fixation techniques, the drill guide being universally adjustable over all typical bone staple sizes.

In yet a further aspect, the present invention provides a drill guide for use in bone fixation surgery employing bone staples or the like, wherein the depth of the holes in the bone(s) can be accurately controlled.

These and further features and advantages of the present invention will become apparent from the following detailed description, wherein reference is made to the figures in the accompanying drawings.

BRIEF DESCRIPTION OF THE DRAWINGS

FIG. 1 is a front elevational view of the drill guide of the present invention.

FIG. 2 is a side elevational view, partly in section, taken along the lines 2-2 of FIG. 1.

FIG. 3 is a view similar to FIG. 1 showing the drill guide adjusted to a different position for use with a different sized bone staple.

FIG. 4 is a view similar to FIG. 1 showing the drill guide adjusted to yet another position for use with yet a different sized bone staple.

DETAILED DESCRIPTION OF PREFERRED EMBODIMENTS

Figure 5:
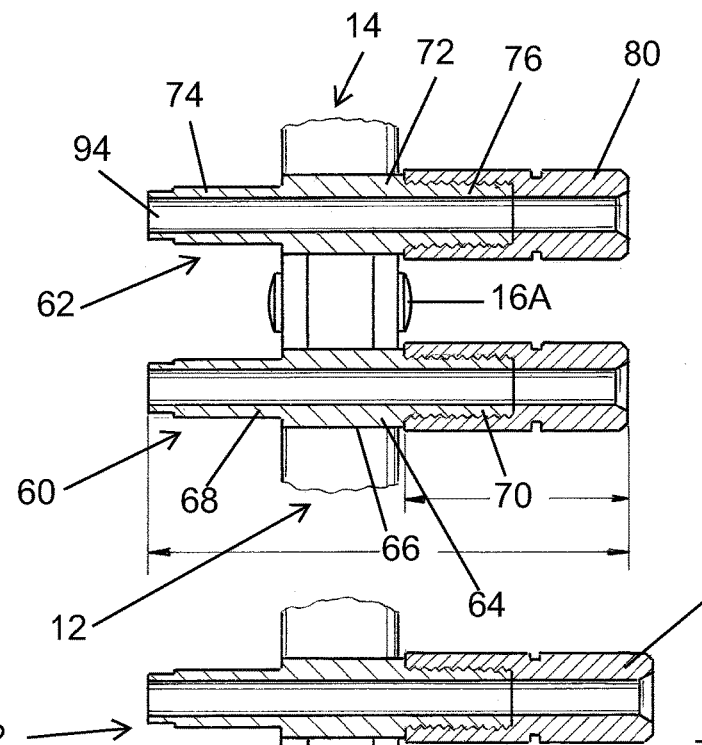
FIG. 5 is a top view, partly in section, of the drill guide shown in FIG. 1, connected to optional spacers for determining drill hole depth.

Referring first to FIG. 1, the drill guide of the present invention shown generally as 10 comprises a first leg 12 having a first end 18 and a second end 20 and a second leg 14 having a first end 26 and a second end 28, legs 12 and 14 being interconnected at a pivot point 16 by means of a pivot pin 16A. The portion of leg 12 below first end 18 and pivot point 16 forms a handle 22, while the portion of leg 12 between second end 20 and pivot point 16 forms a jaw 24. In like fashion, the portion of leg 14 between pivot point 16 and first end 26 forms a handle 30 while the portion of leg 14 between pivot point 16 and second end 28 forms a second jaw 32.

A first cantilevered or flat spring 34 is connected to the inner surface handle 22 of leg 12 by means of a screw 36 while a second cantilevered or flat spring 38 is connected to the inner surface of leg 30 by a similar screw 40. Springs 34 and 38 are interconnected to one another at a juncture 42 located between the handle portions 22 and 30 of legs 12 and 14. It will thus be seen that springs 38 and 34 serve to bias legs 12 and 14 away from one another such that a gripping force applied to handles 22 and 30 is necessary to move the legs 12 and 14 toward one another. Although the embodiment shown in FIG. 1 employs cantilevered or flat springs, it will be apparent to those skilled in the art that numerous other spring mechanisms or biasing systems could be employed.

With reference now to FIG. 2, it can be seen that at the location of pivot point 16, first leg 12 has a pair of spaced laterally inwardly projecting ears 46 and 48 having registering holes for receipt of pivot pin 16A, while second leg 14 has a laterally inwardly projecting flange portion 50 provided with an aperture 52, aperture 52 and the holes in ears 46 and 48 being in register whereby pivot pin 16A can be received therein.

There is a first drill guide, shown generally as 60, proximal end 20 of leg 12 and a second drill guide, shown generally as 62, proximal end 28 of leg 14. As best seen with reference to FIGS. 2 and 5-7, the drill guides 60 and 62 are of substantially the same construction. In this regard, drill guide 60 comprises a tubular member 64 received through bore 66 formed in the jaw portion 24. Tubular member 64 can be press-fitted into bore 66 or welded to jaw member 24 or connected in any other suitable fashion. In any event, tubular member 64 includes a nose portion 68 which protrudes laterally outwardly from jaw portion 24 of leg 12 and optionally a threaded male connector portion 70 which projects laterally outwardly from jaw 24 in a direction opposite to the direction of nose portion 68. In like fashion, guide 62 includes a tubular member 72 received through bore 23 in jaw portion 32, tubular member 72 having a nose portion 74 and a male threaded connector portion 76. In effect, nose portions 68 and 74 as well as connector portions 70 and 74 project away from jaw portions 24 and 32 in a direction generally transverse to a plane passing through legs 12 and 14.

Jaw 14 has a laterally inwardly extension 100 to which is pivotally secured via pivot pin 102, a graduated bar 104. As shown in FIG. 1, graduated bar 104 has a series of longitudinally spaced saw tooth shaped grooves, the spacing between various combinations of the grooves generally corresponding to the width of bone staples commonly used in bone fixation surgery. As shown, first end 18 of leg 12 has a tapered tip 108 received in one of the saw tooth shaped grooves 106. It will be appreciated that since graduated bar 104 is pivotally secured to second leg 14, if it is swung down and away from first end 18 of leg 12 in the direction of arrow A, legs 12 and 14 can move away from one another to the point where the jaws 24 and 32 engage. Accordingly, when it is desired to space the jaws 24 and 32 a desired distance apart to drill the holes for a desired staple size, the surgeon would grasp the legs 12 and 14, clamp them together until the tapered or feathered edge 108 of first end 18 of leg 12 was in register with the desired saw tooth shaped groove 106. Once the feathered or tapered edge 108 of first end 18 of leg 12 was received in the desired groove 106, the gripping force could then be released and under the biasing influence of the spring members 34 and 38, the spacing between the drill guides 60 and 62 would stay fixed while the drilling was performed.

It will be appreciated that the graduated bar 104 is simply one example of an indexing member or assembly which could be used to releasably, selectively fix the spacing between the first ends 18 and 26 of legs 12 and 14, respectively, and then latch, catch or hold the relative positions of the legs 12 and 14 such that the spacing between the drill guides 60 and 62 remain constant.

As noted above, the male connectors 70 and 76 are optional in that they are only necessary if it is desired to use spacers to control the depth of the borehole formed by the drill during the drilling process. Furthermore, while shown as male threaded connectors, it will be apparent that the connectors 70 and 76, when employed, could take various configurations which would allow spacers to be attached thereto. For example, the connectors 70 and 76 could have a bayonet or J-slot connections with spacers designed to fit those bayonet or J-slot formations. Additionally, any quick connect structure could be employed.

As shown, connector 70 has threadedly received thereon a spacer 78 provided with internal, female threads, which mate with the threads on threaded connector 70 while there is a second spacer 80 which also has internal female threads to mate with the threads on threaded connector 76.

Figure 6:
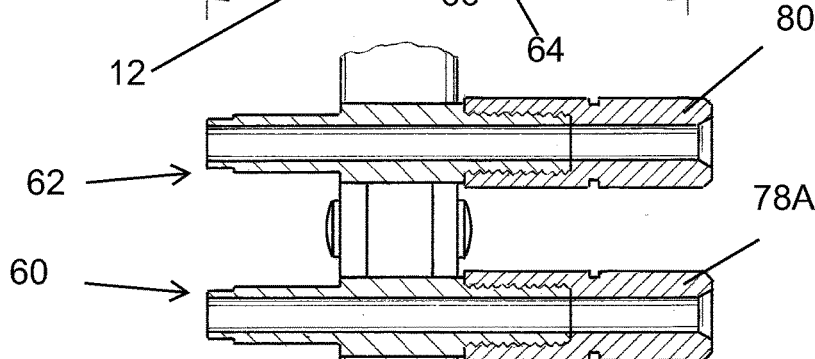
FIG. 6 is a view similar to FIG. 5 showing the use of another size spacer.

It will be apparent that the spacers 78 and 80 can be of any desired length and in this regard, reference is made to FIG. 6 which shows spacers 78A and 80A which are longer than spacers 78 and 80, respectively. While in both FIGS. 5 and 6, the spacers are shown as being of equal length, it will be understood that in certain instances, it may be desired that only one spacer is used or that the two spacers be of different lengths.

While the drill guides 60 and 62 have been described with respect to protruding nose portions 68 and 74, respectively, it will be understood that such nose portions could be dispensed with and the drill guide holes formed simply by bores extending through the jaws 24 and 32. However, such a structure would be less desirable since bone(s) surfaces are generally not sufficiently flat to ensure that the drill guide holes could be placed adjacent the bone surface(s).

Figure 7:
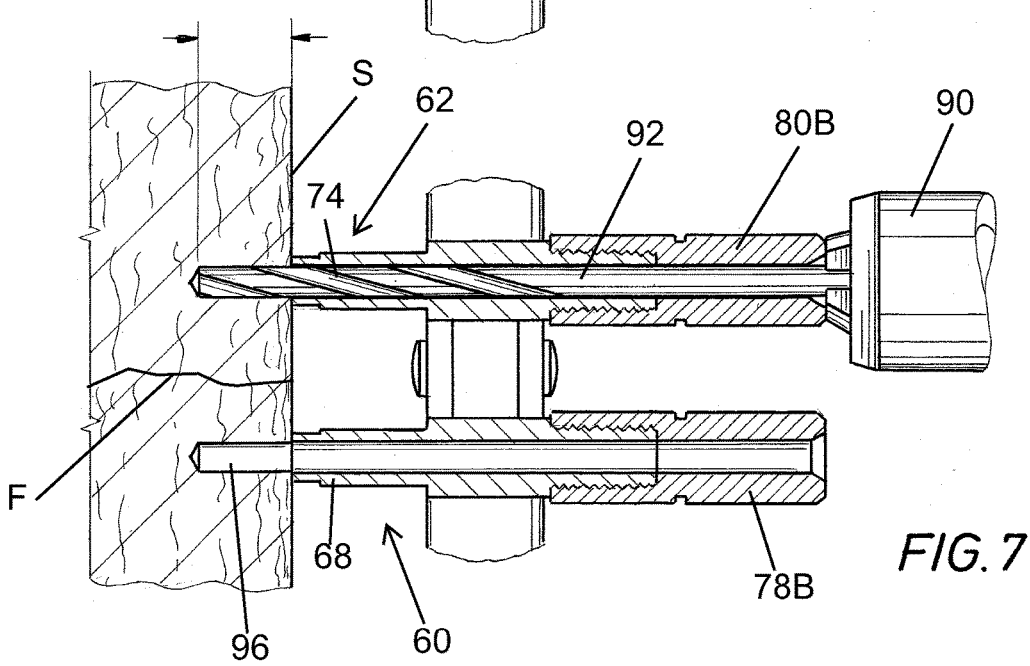
FIG. 7 is an environmental view showing the use of the drill guide to form drill holes in a bone having a fracture.

Turning now to FIG. 7, there is shown the use of the drill guide of the present invention in drilling holes in a bone having a fracture, the holes being drilled for receipt of the legs of a compression type staple, e.g., a memory metal staple. As seen in FIG. 7, nose portions 68 and 74 would be placed against the bone surface S, the nose portions 68 and 74 being positioned on either side of a bone fracture shown schematically as F. Once positioned, a drill 90 having a drill bit 92 conventionally used in bone surgical procedures, would be placed through the throughbore 94 formed by registering bores in connector 80 and nose portion 78. As shown, the drill bit 92 has been drilled into the bone to the maximum depth, spacer 80 serving as a stop to limit the depth of the hole in the bone, one such hole having already been drilled as shown at 96. It will be observed that the spacers 78B and 80B shown in FIG. 7 are longer than those shown in either FIG. 5 or 6.

It will be apparent that the drill guide of the present invention provides several distinct advantages over prior art drill guides. For one, using a single instrument, the surgeon has adjustability to all of the staple sizes commonly used in bone fixation surgery. Additionally, because of the optional spacers, the depth of one or both of the holes to be drilled can be quickly and accurately varied.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A drill guide for use in positioning the location of holes to be drilled in a bone for the insertion of bone staples, said guide comprising:

first and second legs, each of said legs having a first end and a second end;

a pivot connecting said first and second legs together at a pivot point;

first and second jaws formed from portions of said first and second legs extending from said pivot point to said second ends, first and second handles formed from portions of said first and second legs extending from said pivot point to said first ends;

said first jaw having a first drill guide proximal said second end of said first leg, said second jaw having a second drill guide proximal said second end of said second leg, said first and second drill guides having first and second guide bores, said guide bores having first and second axes extending therethrough, said first and second axes being generally transverse to a plane passing through said first and second legs and said pivot, said first and second drill guides comprising first and second connector portions extending laterally outwardly, said first and second connector portions having male threads;

at least one drill guide spacer having female threads for selectively releasably attaching to said male threads of one of said first or second connector portions, said at least one drill guide spacer having a through bore in register with said first or second guide bores to increase the effective length of said first or second guide bores and act as a stop for a drill;

an indexer operatively connected to said first and second legs and including a biaser and a unitary latch, said unitary latch being connected to both first and second legs;

said biaser being connected to both first and second legs and operative to bias said first ends of said first and second legs in a direction away from each other; and said latch selectively, releasably holding said first and second legs in a predetermined, desired spacing.

2. The drill guide of claim 1, wherein said pivot point is more proximal said second ends than said first ends.

3. The drill guide of claim 1, wherein said first leg has a pair of spaced ears projecting inwardly toward said second leg and forming a slot therebetween, said ears having first and second registering holes, said second leg having a flange projecting toward said first leg, said flange having an aperture therethrough, said flange being received in said slot, said aperture and said holes being in register and, said pivot comprising a pivot pin extending through said registering holes and aperture.

4. The drill guide of claim 1, wherein each of said drill guides comprise first and second nose portions, respectively, extending in a first direction away from said first and second legs for engaging said bone to be drilled.

5. The drill guide of claim 4, wherein each of said first and second connector portions extend in a second opposite direction from said first and second legs.

6. The drill guide of claim 1, wherein there are two of said drill guide spacers.

7. The drill guide of claim 6, wherein the two spacers are of differing lengths.

8. The drill guide of claim 1, wherein said biaser comprises a first cantilevered spring member connected to said first leg and a second cantilevered spring member connected to said second leg, said first and second cantilevered spring members each having free end portions connected to each other between said first and second legs.

9. The drill guide of claim 8, wherein said first end of said first leg is wedge shaped.

10. The drill guide of claim 1, wherein said latch comprises a graduated bar having a first end pivotally connected to said second leg, said graduated bar comprising a series of longitudinally spaced notches, said notches being selectively engageable by said first leg at a preselected location.

11. A drill guide for use in positioning the location of holes to be drilled for the insertion of bone staples, said guide comprising:

first and second legs, each of said legs having a first end and a second end;

a pivot connecting said first and second legs together at a pivot point;

first and second jaws formed from portions of said first and second legs extending from said pivot point to said second ends, first and second handles formed from portions of said first and second legs extending from said pivot point to said first ends;

said first jaw having a first drill guide proximal said second end of said first leg, said second jaw having a second drill guide proximal said second end of said second leg, said first and second drill guides having first and second guide bores, said guide bores having first and second axes extending therethrough, said first and second axes being generally transverse to a plane passing through said first and second legs and said pivot, said first and second drill guides comprising first and second connector portions extending laterally outwardly, said first and second connector portions having male threads;

at least one drill guide spacer having female threads for selectively releasably attaching to said male threads of one of said first or second connector portions, said at least one drill guide spacer having a through bore in register with said first or second guide bores to increase the effective length of said first or second guide bores and act as a stop for a drill;

an indexer for selectively, releasably holding said first and second legs in a predetermined, desired spacing and including a biaser and a unitary latch, said unitary latch being directly connected to said first and second legs; and said biaser being operative to bias said first ends of said first and second legs in a direction away from each other.

12. The drill guide of claim 11, wherein said pivot point is more proximal said second ends than said first ends.

13. The drill guide of claim 11, wherein said first leg has a pair of spaced ears projecting inwardly toward said second leg and forming a slot therebetween, said ears having first and second registering holes, said second leg having a flange projecting toward said first leg, said flange having an aperture therethrough, said flange being received in said slot, said aperture and said holes being in register and, said pivot comprising a pivot pin extending through said registering holes and aperture.

14. The drill guide of claim 11, wherein each of said drill guides have first and second nose portions, respectively, extending in a first direction away from said first and second legs for engaging said bone to be drilled.

15. The drill guide of claim 14, wherein each of said first and second connector portions extends in a second opposite direction from said first and second legs.

16. The drill guide of claim 11, wherein there are two of said drill guide spacers.

17. The drill guide of claim 16, wherein the two spacers are of differing lengths.

18. The drill guide of claim 11, wherein said biaser comprises a first cantilevered spring member connected to said first leg and a second cantilevered spring member connected to said second leg, said first and second cantilevered spring members each having free end portions connected to each other between said first and second legs.

19. The drill guide of claim 11, wherein said latch comprises a graduated bar having a first end pivotally connected to said second leg, said graduated bar comprising a series of longitudinally spaced notches, said notches being selectively engageable by said first leg at a preselected location.

20. The drill guide of claim 19, wherein said first end of said first leg is wedge shaped.

* * * * *